US009102762B2

(12) United States Patent
Christensen et al.

(10) Patent No.: US 9,102,762 B2
(45) Date of Patent: Aug. 11, 2015

(54) VIRUS FILTRATION OF LIQUID FACTOR VII COMPOSITIONS

(75) Inventors: Jesper Christensen, Gentofte (DK); Erik Halkjær, Copenhagen N (DK); Turid Preuss, Smørum (DK); Thomas Budde Hansen, Copenhagen N (DK); Lene Vædele Madsen Tomoda, Lyngby (DK); Nina Johansen, Rødovre (DK)

(73) Assignee: Novo Nordisk Healthcare AG, Zurich (CH)

( * ) Notice: Subject to any disclaimer, the term of this patent is extended or adjusted under 35 U.S.C. 154(b) by 818 days.

(21) Appl. No.: 13/349,980

(22) Filed: Jan. 13, 2012

(65) Prior Publication Data

US 2012/0115204 A1     May 10, 2012

Related U.S. Application Data (63) Continuation of application No. 12/173,475, filed on Jul. 15, 2008, now abandoned, and a continuation of application No. 11/439,828, filed on May 23, 2006, now abandoned, which is a continuation of application No. PCT/DK2004/053206, filed on Dec. 1, 2004.

(60) Provisional application No. 60/528,763, filed on Dec. 11, 2003.

(30) Foreign Application Priority Data

Dec. 1, 2003   (DK) .................................. 2003 01775

(51) Int. Cl.
*C07K 14/745* (2006.01)
*C12N 7/00* (2006.01)
*C12N 9/64* (2006.01)

(52) U.S. Cl.
CPC ............... *C07K 14/745* (2013.01); *C12N 7/00* (2013.01); *C12N 9/6437* (2013.01); *C12Y 304/21021* (2013.01); *C12N 2740/13063* (2013.01)

(58) Field of Classification Search
None
See application file for complete search history.

(56) References Cited

U.S. PATENT DOCUMENTS

| | | | |
|---|---|---|---|
| 5,677,162 A † | 10/1997 | Zou et al. | |
| 5,997,864 A | 12/1999 | Hart et al. | |
| 6,100,061 A | 8/2000 | Reiter et al. | |
| 6,777,390 B1 | 8/2004 | Matthiessen et al. | |
| 2001/0051154 A1 | 12/2001 | Roemisch et al. | |
| 2003/0232969 A1 | 12/2003 | Lengsfeld et al. | |
| 2005/0192223 A1 | 9/2005 | Eibl | |
| 2006/0166882 A1 | 7/2006 | Jensen et al. | |
| 2009/0239788 A1 | 9/2009 | Chtourou et al. | |
| 2009/0281283 A1 | 11/2009 | Lejars et al. | |
| 2009/0311239 A1 | 12/2009 | Chtourou et al. | |
| 2010/0047428 A1 | 2/2010 | Lejars et al. | |
| 2012/0087908 A1 | 4/2012 | Bardat et al. | |

FOREIGN PATENT DOCUMENTS

| | | |
|---|---|---|
| DK | PA 2003 01775 | 12/2004 |
| EP | 131740 | 10/1990 |
| EP | 549964 | 12/1992 |
| EP | 1029546 A1 | 8/2000 |
| EP | 1348445 A1 | 10/2003 |
| EP | 2275432 A1 | 1/2011 |
| EP | 2687595 A1 | 1/2014 |
| FR | 2901707 A1 | 12/2007 |
| FR | 2901796 A1 | 12/2007 |
| FR | 2904558 A1 | 2/2008 |
| FR | 2910786 A1 | 7/2008 |
| FR | 2947181 A1 | 12/2010 |
| JP | 2001521941 A | 11/2001 |
| KR | 20070001887 A | 1/2007 |
| KR | 20090028694 A | 3/2009 |
| KR | 20090031676 A | 3/2009 |
| KR | 20090040892 A | 4/2009 |
| KR | 20090113825 A | 11/2009 |
| KR | 20120047918 A | 5/2012 |
| KR | 1234170 | 2/2013 |
| KR | 20147022570 | 11/2014 |
| WO | 92/15686 A1 | 9/1992 |
| WO | 94/22905 A1 | 10/1994 |
| WO | WO96/00237 | 1/1996 |
| WO | WO 98/37086 | 8/1998 |
| WO | 9922753 A1 | 5/1999 |
| WO | 99/64441 A1 | 12/1999 |
| WO | 99/66031 A2 | 12/1999 |
| WO | 02/29084 A2 | 4/2002 |
| WO | 2004011024 A1 | 2/2004 |
| WO | 2005/054275 A2 | 6/2005 |

OTHER PUBLICATIONS

Guidelines on the selection and use of therapeutic products to treat haemophilia and other hereditary bleeding disorders. Haemophilia 2003 vol. 9: 1-23.
Persson et al FEBS Letters vol. 413: 359-363 (1997).
Persson et al. J Biol Chem vol. 272: 19919-19924 (1997).
Fenaille et al "Mass spectrometric characterization of N- and O-glycans of plasma-derived coagulation factor VII" Glycoconj. J vol. 25: 827-842. 2008.
Protocol of Asserachrom kit. 2010.
Protocol of Staclot kit. Apr. 2010.
Declaration of Nicolas Bihoreau. Jul. 2014.
Guidance for Industry, "Q5A Viral Safety Evaluation of Biotechnology Products Derived From Cell Lines of Human or Animal Origin", U.S. Department of Health and Human Services, 1998, p. 1-33.

(Continued)

*Primary Examiner* — Anand Desai
(74) *Attorney, Agent, or Firm* — Nonna G. Akopyan (57) ABSTRACT

The present invention relates to a novel method for improving the viral safety of liquid Factor VII compositions, in particular those comprising active Factor VII polypeptides (a Factor VIIa polypeptide).

15 Claims, 1 Drawing Sheet

(56) References Cited

OTHER PUBLICATIONS

European Medicines Agency, "Guideline on Virus Safety Evaluation of Biotechnological Investigational Medicinal Products", 2008, p. 1-9.
Claimant's additionally experimental data and translation thereof.
Hirasaki T H et al.Effects of Varing Virus-Spiking Conditions on a Virus-Removal Filter PlanovaTM 20N in a Virus Validation Study of Antibody Solution,Journal : Biotechnol prog ,Year 2011, vol. 27, No. 1 pp. 162-169.
Naito Y et al.,Virus removal from hemoglobin solution using Planova Membrane, Journal :Japanese Society of artificial organs, Year 2002. vol. 5 , pp. 141-145.
Roberts P L et al.Virus removal from factor IX by filtration: Validation of the integrity test and effect of manufacturing process conditions, Journal :Biologicals, Year 2010, vol. 38. pp. 303-310.
Exhibit 14—Summary of product characteristics. Downloaded document from the website of European commision. ec.europa.eu/health/documents/community-register/html/h006.htm.
Radcliffe et al., "Activation and Control of Factor VII by Activated Factor X and Thrombin", The Journal of Biological Chemistry, 1975, vol. 250, No. 2, pp. 388-395.
Thim et al., "Amino Acid Sequence and Posttransitional Modifiactions of Human Factor VIIa From Plasma and Transfected Baby Hamster Kidney Cells", Biochemistry, 1988, Vol. 27, pp. 7785-7793.
Pedersen et al., "Autoactivation of Human Recombinant Coagulation Factor VII", Biochemistry, 1989, vol. 28, pp. 9331-9336.
Chamouard et al., "Le Facteu VII Active Recombinant Eptacog Alpha (Active): Novoseven", 2000, vol. 51, No. 3, pp. 145-163.
Samama, C.M., "Prothrombin Complex Concentrates: A Brief Review", European Journal of Anaesthesiology, 2008, vol. 25, No. 10, pp. 784-789.
Tomokiyo, K. et al., Large-scale production and properties of human plasma-derived activated Factor VII concentrate, Vox Sanguinis, 2003, 54-64, vol. 84.
Burnouf, T. et al., Nanofiltration of plasma-derived biopharmaceutical products, Haemophilia, 2003, 24-37, vol. 9, Blackwell Publishing.
Eigenbrot, Charles, Structure Function and Activation of Coagulation Factor VII, Current Protein and Peptide Science, 2002, 287-299, vol. 3, Bentham Science Publishers.
Horowitz, B. et al., Virus Inactivation by Solvent/Detergent Treatment and the Manufacture of SD-Plasma, Vox Sanguines, 1998, 203-206, vol. 74, No. 1.
Chandra, S. et al., Effectiveness of Alternative treatments for reducing potential viral contaminants from plasma-derived products, Thrombosis Research, 2002, 391-400, vol. 105, Elsevier Science Ltd.
Josic et al., Manufacturing of a prothrombin complex concentrate aiming at low thrombogenicity, Thrombosis Research 100: 433-441, 2000.
O'Grady et al., Virus removal studies using nanofiltration membranes, Brown F., Lubiniecki AS: Viral Safety and Evaluation of Viral Clearance from Biopharmaceutical Products, Dev. Biol. Stand., Basel Karger, vol. 88, pp. 319-326, 1996.
Oda et al., PDA Journal of GMP and Validation in Japan, 2002, vol. 4, No. 1, pp. 54-64.
Radosevich et al., Journal of Chromatography, 2003, Vol. 790, pp. 199-207.
Mollerup et al., Biotechnology and Bioengineering, 1995, vol. 48, No. 5, pp. 501-505.
Pall Corporation, ULTIPOR® VF Grade DV50 Virus Removal Filter Cartridges, pp. 1-3, Oct. 31, 2011.
Product Monograph, Feiba NF, "Anti-Inhibitor Coagulant Complex, Vapor Heated and Nanofiltered Freeze-Dried Substance With Solvent for Intravenous Injection or Infusion", Baxter Corporation, pp. 1-34, Jul. 5, 2011.
ODA, PDA Journal of GMP and Validation in Japan, "Points to Consider for Virus and DNA Removal Using Membranes During the Scale-Up of Biopharmaceutical Drug Development", 2002, vol. 4, No. 1, pp. 26-34.
Jurlander B, et al. Recombinant Activated FActor VII (rFVIIa): Characterization, Manufacturing, and Clinical Development. Seminars in Thrombosis and Hemostasis 2001; vol. 27, No. 4: 373-383.
Declaration by Charnouard V.and the publisher certifying the publication date for Lyon pharmaceutigue 2000, vol. 51, No. 3, pp. 145-163 on Apr. 8, 2013.
Declaration by Magali Andre for Fig 4 of Tomokiyo et al, Vox sanguinis 2003 vol. 84 No. 1 pp. 54-64 , on Mar. 25, 2015.
Tsurumi T et al,Structure of Cuprammonium Regenerated Cellulose Hollow Fiber (BMM Hollow Fiber) for Virus Removal,Polymer Journal, 1990,vol. 22, No. 8, pp. 751-758.
Brorson et al., Nomenclature Standardization for "Large Pore Size" Virus-Retentive Filters, Bioprocess International, Nov. 2005, pp. 21-23 (supplement).
Assessment information "Scientific Discussion" on Eptacog Alpha (Novoseven) from EMA website, accessed Mar. 18, 2015.
Millepore, Viresolve NFP Filter Data Sheet, copyrighted 2003, 2005, 2006, 2007.
Merck Millepore, Viresolve NFR Filters Data Sheet, copyrighted 2012.
Kaufman et al., Expression, Purification, and Characterization of Recombinant a-Carboxylated Factor IX Sythensized in Chinese Hamster Ovary Cells, The Journal of Biological Chemistry, 1986 vol. 261 No. 21, pp. 9622-9628.
SPC (Summary of Product Characteristics, pp. 1-12) Eptacog Alpha (Novoseven®), from EMA website, accessed Mar. 18, 2015.
Chamouard, V. et al. Recombinant Activated Factor VII Eptacog Alpha (Activated): Novoseven®, Lyon Pharmaceutique 2000, 51(3), pp. 145-163 Translation.
Chamouard et al., "Recombinant Activated Factor VII Eptacog Alpha (Activated): Novoseven," 145-163, 2000, Lyon Pharmaceutique.†
Burnouf et al., "Nanofiltration of plasma-derived biopharmaceutical products," 24-37, 2003, Haemophilia.†
Pall Corporation, "Ultipor VF Grade DV50 Virus Removal Filter Cartridges," 3 pages, Oct. 18, 2011.†
Baxter AG, "Product Monograph—Feiba NF", 34 pages, Jul. 5, 2011.†
Josic et al., "Manufacturing of a Prothrombin Complex Concentrate Aiming at Low Thrombogenicity," 2000, 433-441, Thrombosis.†
Tomokiyo et al., "Large-scale production and properties of human plasma-derived activated Factor VII concentrate," 2003, 54-64, Vox Sanguinis.†
Hill, "Guidelines on the Selection and Use of Therapeutic Products to Treat Haemophilia and Other Hereditary Bleeding Disorders," Haemophilia (2003), 9, 1-23.†

† cited by third party

VIRUS FILTRATION OF LIQUID FACTOR VII COMPOSITIONS

CROSS-REFERENCE TO RELATED APPLICATIONS

This application is a continuation of U.S. patent application Ser. No. 12/173,475, filed Jul. 15, 2008, which is a continuation of U.S. patent application Ser. No. 11/439,828, filed May 23, 2006, which is a continuation of International Patent Application No. PCT/DK04/53206, filed Dec. 1, 2004, which claims priority from Danish Patent Application No. PA 2003 01775, filed Dec. 1, 2003; and to U.S. Patent Application No. 60/528,763, filed Dec. 11, 2003.

FIELD OF THE INVENTION

The present invention relates to a novel method for improving the viral safety of liquid Factor VII compositions, in particular those comprising active Factor VII polypeptides (a Factor VIIa polypeptide).

BACKGROUND OF THE INVENTION

A variety of Factors involved in the blood clotting process have been identified, including Factor VII (FVII), a plasma glycoprotein. Haemostasis is initiated by the formation of a complex between Tissue Factor (TF) being exposed to the circulating blood following an injury to the vessel wall, and Factor VIIa which is present in the circulation in an amount corresponding to about 1% of the total Factor VII protein mass. Factor VII exists in plasma mainly as a single-chain zymogen which is cleaved by FXa into its two-chain, activated form, Factor VIIa. Recombinant activated Factor VIIa (rFVIIa) has been developed as a pro-haemostatic agent. The administration of rFVIIa offers a rapid and highly effective pro-haemostatic response in haemophilic subjects with bleedings, who cannot be treated with other coagulation Factor products due to antibody formation. Also bleeding in subjects with Factor VII deficiency or subjects having a normal coagulation system but experiencing excessive bleeding can be treated successfully with Factor VIIa.

The purification and handling of Factor VII must be careful, due the possibility for degradation of the molecule. Factor VII and Factor VIIa, being large molecules (approx. molecular weight 50 kD), are susceptible to mechanical degradation by shear forces during purification and filtration. Further, Factor VIIa is an active proteolytic enzyme that degrades other proteins including Factor VIIa. Degradation of Factor VIIa mainly involves cleavage in the heavy chain of Factor VIIa, particularly at amino acids no. 290 and 315 in the molecule. Finally, methionine residues in Factor VII and Factor VIIa may be oxidized.

An object of the present invention is to provide a method for the removal or inactivation of viruses from liquid Factor VII compositions by which method the integrity of the Factor VII constituents is substantially preserved.

WO 96/00237 discloses a method of virus-filtration of a solution that contains a macromolecular, e.g. a protein such as the plasma protein Factor IX.

WO 98/37086 discloses removal of viruses from plasma-derived protein solutions by nanofiltration using a membrane having an average pore size of 15 nm.

Tomokiyo et al., Vox Sanguinis, 2003, 84, 54-64, disclose the large-scale production of human plasma-derived activated Factor VII concentrate. The method of production involves the step of virus-filtration of a solution comprising inactive Factor VII.

BRIEF DESCRIPTION OF THE INVENTION

In a broad aspect, the preset invention relates to methods for the removal and/or inactivation of viruses from Factor VII composition. The term "virus" as used herein means any ultramicroscopic infectious agent that replicates itself only within cells of living hosts, or noninfectious particles derived thereof. In one embodiment the virus is infectious. In one embodiment the virus is a non-infectious virus particle.

A first aspect of the present invention relates to a method for removing viruses from a liquid Factor VII composition, said method comprising subjecting said solution to nanofiltration using a nanofilter having a pore size of at the most 80 nm.

A second aspect of the present invention relates to a method for removing viruses from a liquid Factor VII composition, said composition comprising one or more Factor VII polypeptides, at least 5% of said one or more Factor VII polypeptides being in the activated form, said method comprising subjecting said solution to nanofiltration using a nanofilter having a pore size of at the most 80 nm.

A third aspect of the invention relates to a method for removing viruses from a liquid Factor VII composition, said composition comprising one or more Factor VII polypeptides, said liquid composition being substantially serum-free, said method comprising subjecting said solution to nanofiltration using a nanofilter having a pore size of at the most 80 nm.

A further aspect of the invention relates to a method for removing viruses from a liquid Factor VII composition, said composition comprising one or more Factor VII polypeptides, said method comprising subjecting said solution to nanofiltration using a nanofilter having a pore size of at the most 80 nm, said nanofilter having a membrane manufactured from one or more materials selected from cuprammonium regenerated cellulose, hydrophilic polyvinylidene fluoride (PVDF), composite PVDF, surface modified PVDF, and polyether sulfone.

A further aspect of the invention relates to a method for inactivating viruses in a liquid Factor VII composition, said composition comprising one or more Factor VII polypeptides, the method comprising the step of combining said composition with a detergent.

A further aspect of the invention relates to a method for high-level elimination of the presence of active viruses in a liquid Factor VII composition, the method comprising the steps of (i) inactivating viruses, and (ii) removing viruses.

BRIEF DESCRIPTION OF THE DRAWINGS

FIG. 1 is a schematic illustration of a system suitable for methods of the invention. The system includes a pressure tank (1) with a supply of compressed air, a pre-filter (2) for removing particles that would otherwise clog the virus filter, a pressure gauge (P), a virus filter (3), and a pool tank (4).

DETAILED DESCRIPTION OF THE INVENTION

The present invention provides methods for removing or inactivating viruses, including non-enveloped viruses, from a liquid Factor VII composition which typically comprises a significant ratio of activated and thereby proteolytically active Factor VII polypeptides. The method includes the step of subjecting the liquid Factor VII composition to nanofiltration using a nanofilter having a pore size of at the most 80 nm.

The method is particularly useful for the removal of enveloped viruses as well as non-enveloped viruses such as Murine Leukemia virus (enveloped) which may be removed by filters with a pore size around 50 nm, and Porcine Parvovirus (non-enveloped) which may be removed by filters with a pore size around 20 nm.

The liquid Factor VII compositions, e.g. those comprising a significant ratio of activated Factor VII polypeptides, can in principle be prepared from the dry Factor VII constituents, but are more typically obtained from large-scale production processes, e.g. processes involving recombinant techniques. In such processes a cell culture supernatant is typically harvested and subsequently subjected to one or more processing steps to obtain the desired protein, including, without limitation, centrifugation or filtration to remove cells that were not immobilized in the carriers; affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989. Purification of Factor VII polypeptides may also involve, e.g., affinity chromatography on an anti-Factor VII antibody column (see, e.g., Wakabayashi et al., *J. Biol. Chem.* 261:11097, 1986; and Thim et al., *Biochem.* 27:7785, 1988) and activation by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, a Factor VII polypeptide may be activated by passing it through an ion-exchange chromatography column, such as Mono Q® (Pharmacia) or the like.

The methods of the present invention are particularly useful for large-scale production processes. By the term "large-scale" is typically meant methods wherein the volume of the liquid Factor VII polypeptide compositions is at least 100 L, such as at least 500 L, e.g. at least 1000 L, or at least 5000 L. This is not to be limiting in any way, as the present invention will also work for liquid Factor VII polypeptide compositions of less than 100 L.

It has now been realized that nanofiltration may be applied even after the Factor VII polypeptide bulk has been partially or fully activated.

Thus, the methods of the invention are applicable as one of the steps of the overall purification process for the Factor VII polypeptide, typically one of the final steps of the purification process.

More specifically, a typical purification process starting from harvested material from the a fermentation broth (or from human (or mammalian) plasma) can be outlined as follows:

| Purification step | Possible stages for virus filtration |
| --- | --- |
| Harvest ↓ | 1 |
| Capture ↓ | 2 |
| Intermediate purification ↓ | 3 |
| Polishing ↓ Drug substance | 4 |

The content of Factor VII polypeptide in the activated form is initially (i.e. from the harvest step) typically around 2%, and increases in the course of the purification process to 90% or more before the polypeptide is obtained as a drug substance.

The liquid Factor VII composition subjected to nanofiltration comprises one or more Factor VII polypeptides in a suitable solvent. The solvent is typically water or an aqueous mixture/solution, such as pure water, an aqueous buffer, a water/ethanol mixture, a water/DMSO mixture, or an aqueous salt solution, e.g. saline, a urea solution or guanidine solution. A suitable aqueous liquid may also comprise a detergent (surfactant).

In interesting embodiments, the liquid Factor VII composition is obtained, or originates, from a cell culture supernatant, e.g. a cell culture supernatant obtained as disclosed in WO 02/29084. In one embodiment, the liquid Factor VII composition is serum-free, i.e. free from animal-derived components. Thus, the cell cultures may be cultivated in a medium lacking animal derived components.

An attractive variant hereof is the one where the Factor VII polypeptide(s) is/are produced by cell culture in CHO cells, e.g. in CHO cells in a medium free from any components of animal origin, or a medium lacking animal-derived components and lacking proteins ("protein-free").

The medium for CHO cells may be any commercially available protein-free CHO medium lacking animal-derived components or an in-house produced medium for CHO cells.

In some embodiments, the cells used in practicing the present invention are adapted to suspension growth in medium lacking animal-derived components, such as, e.g., medium lacking serum. Such adaptation procedures are described, e.g., in Scharfenberg, et al., *Animal Cell Technology Developments towards the 21st Century*, E. C. Beuvery et al. (Eds.), Kluwer Academic Publishers, pp. 619-623, 1995 (BHK and CHO cells); Cruz, *Biotechnol. Tech.* 11:117-120, 1997 (insect cells); Keen, *Cytotechnol.* 17:203-211, 1995 (myeloma cells); Berg et al., *Biotechniques* 14:972-978, 1993 (human kidney 293 cells). In a particularly embodiment, the host cells are BHK 21 or CHO cells that have been engineered to express human Factor VII or a Factor VII polypeptide and that have been adapted to grow in the absence of serum or animal-derived components.

In an alternative embodiment, the Factor VII polypeptide(s) is/are produced by cell culture in the presence of bovine or fetal calf serum.

According to one aspect of the invention, a feature is that a significant ratio, i.e. at least 5%, such as at least 7%, e.g. at least 10%, of the one or more Factor VII polypeptides are in the activated form (i.e. the bioactive, cleaved form of a Factor VII polypeptide (i.e. a Factor VIIa polypeptide)). In further embodiments, the Factor VIIa polypeptide represents 5-70%, such as 7-40%, e.g. 10-30%, of the mass of the one or more Factor VII polypeptides. In other embodiments, the Factor VIIa polypeptide represents 50-100%, such as 70-100%, e.g. 80-100%, of the mass of the one or more Factor VII polypeptides. In still other embodiments, the Factor VIIa polypeptide represents 20-80%, such as 30-70%, e.g. 30-60%, of the mass of the one or more Factor VII polypeptides.

In most embodiments, the solution comprises a Factor VII polypeptide in inactivated form as well as a bioactive Factor VIIa polypeptide, i.e. the Factor VIIa polypeptide represents less than 100% of the mass of the one or more Factor VII polypeptides. In the most typical embodiment, the composition comprises a(n) (activated) Factor VIIa polypeptide that corresponds to an (inactive) Factor VII polypeptide, i.e. the Factor VIIa polypeptide is the Factor VII polypeptide in the activated form. In other embodiment, the Factor VIIa polypeptide is somewhat different from the activated form of the inactivated Factor VII polypeptide. It should of course be understood that the composition in particular embodiments may comprise more than one Factor VII polypeptide and more than one Factor VIIa polypeptide.

The term "one or more Factor VII polypeptides" encompasses wild-type Factor VII (i.e. a polypeptide having the amino acid sequence disclosed in U.S. Pat. No. 4,784,950), as well as variants of Factor VII exhibiting substantially the same or improved biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VIIa" specifically means an activated (i.e. bioactive, cleaved) Factor VII polypeptide. Thus, "Factor VIIa" is a subgroup relative to "Factor VII". The term "inactive Factor VII" specifically means Factor VII not being Factor VIIa.

The term "Factor VII polypeptide" also encompasses polypeptides, including variants, in which the Factor VIIa biological activity has been substantially modified or somewhat reduced relative to the activity of wild-type Factor VIIa, as well as Factor VII derivatives and Factor VII conjugates. These polypeptides include, without limitation, Factor VII or Factor VIIa into which specific amino acid sequence alterations have been introduced that modify or disrupt the bioactivity of the polypeptide. The term "Factor VII derivative" as used herein, is intended to designate wild-type Factor VII, variants of Factor VII exhibiting substantially the same or improved biological activity relative to wild-type Factor VII and Factor VII-related polypeptides, in which one or more of the amino acids of the parent peptide have been chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

The biological activity of Factor VIIa in blood clotting derives from its ability to (i) bind to Tissue Factor (TF) and (ii) catalyze the proteolytic cleavage of Factor IX or Factor X to produce activated Factor IX or X (Factor IXa or Xa, respectively).

For the purposes of the invention, biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864 or WO 92/15686. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) measuring the ability of Factor VIIa (or the Factor VII polypeptide) to produce activated Factor X (Factor Xa) in a system comprising TF embedded in a lipid membrane and Factor X. (Persson et al., J. Biol. Chem. 272:19919-19924, 1997); (ii) measuring Factor X hydrolysis in an aqueous system ("In Vitro Proteolysis Assay", see below); (iii) measuring the physical binding of Factor VIIa (or the Factor VII polypeptide) to TF using an instrument based on surface plasmon resonance (Persson, FEBS Letts. 413:359-363, 1997); (iv) measuring hydrolysis of a synthetic substrate by Factor VIIa (or a Factor VII polypeptide) ("In Vitro Hydrolysis Assay", see below); or (v) measuring generation of thrombin in a TF-independent in vitro system.

Factor VII variants having substantially the same or improved biological activity relative to wild-type Factor VIIa encompass those that exhibit at least about 25%, such as at least about 50%, such as at least about 75%, such as at least about 90% of the specific activity of Factor VIIa that has been produced in the same cell type, when tested in one or more of a clotting assay, proteolysis assay, or TF binding assay as described above. In one embodiment the biological activity is more than 80% of the biological activity of recombinant wild type human Factor VIIa. In another embodiment the biological activity is more than 90% of the biological activity of recombinant wild type human Factor VIIa. In a further embodiment the biological activity is more than 100% of the biological activity of recombinant wild type human Factor VIIa. In a further embodiment the biological activity is more than 120% of the biological activity of recombinant wild type human Factor VIIa. In a further embodiment the biological activity is more than 200% of the biological activity of recombinant wild type human Factor VIIa. In a further embodiment the biological activity is more than 400% of the biological activity of recombinant wild type human Factor VIIa.

Factor VII variants having substantially reduced biological activity relative to wild-type Factor VIIa are those that exhibit less than about 25%, such as less than about 10%, such as less than about 5%, such as less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); Factor VIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); Factor VII variants as disclosed in PCT/DK02/00189; and Factor VII variants exhibiting increased proteolytic stability as disclosed in WO 02/38162 (Scripps Research Institute); Factor VII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and Factor VII variants as disclosed in WO 01/58935, U.S. Pat. No. 6,806,063, US patent application 20030096338 (Maxygen ApS), WO 03/93465 (Maxygen ApS) and WO 04/029091 (Maxygen ApS).

Non-limiting examples of Factor VII variants having increased biological activity compared to wild-type Factor VIIa include Factor VII variants as disclosed in WO 01/83725, WO 02/22776, WO 02/077218, WO 03/27147, WO 03/37932; WO 02/38162 (Scripps Research Institute); and Factor VIIa variants with enhanced activity as disclosed in JP 2001061479 (Chemo-Sero-Therapeutic Res Inst.).

Non-limiting examples of Factor VII variants having substantially reduced or modified biological activity relative to wild-type Factor VII include R152E-FVIIa (Wildgoose et al., Biochem 29:3413-3420, 1990), 5344A-FVIIa (Kazama et al., J. Biol. Chem. 270:66-72, 1995), FFR-FVIIa (Hoist et al., Eur. J. Vasc. Endovasc. Surg. 15:515-520, 1998), and Factor VIIa lacking the Gla domain, (Nicoiaisen et al., FEBS Letts. 317:245-249, 1993).

Explicit examples of Factor VII polypeptides include, without limitation, wild-type Factor VII, L305V-FVII, L305V/M306D/D309S-FVII, L3051-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/

L305V/V158D/S314E-FVII, F374Y/L305V/E296V/ M298Q-FVII, F374Y/L305V/E296V/V158T-FVII, F374Y/ L305V/E296V/S314E-FVII, F374Y/L305V/M298Q/ V158T-FVII, F374Y/L305V/M298Q/S314E-FVII, F374Y/ L305V/V158T/S314E-FVII, F374Y/K337A/S314E/V158T-FVII, F374Y/K337A/S314E/M298Q-FVII, F374Y/K337A/ S314E/E296V-FVII, F374Y/K337A/S314E/V158D-FVII, F374Y/K337A/V158T/M298Q-FVII, F374Y/K337A/ V158T/E296V-FVII, F374Y/K337A/M298Q/E296V-FVII, F374Y/K337A/M298Q/V158D-FVII, F374Y/K337A/ E296V/V158D-FVII, F374Y/V158D/S314E/M298Q-FVII, F374Y/V158D/S314E/E296V-FVII, F374Y/V158D/ M298Q/E296V-FVII, F374Y/V158T/S314E/E296V-FVII, F374Y/V158T/S314E/M298Q-FVII, F374Y/V158T/ M298Q/E296V-FVII, F374Y/E296V/S314E/M298Q-FVII, F374Y/L305V/M298Q/K337A/S314E-FVII, F374Y/ L305V/E296V/K337A/S314E-FVII, F374Y/E296V/ M298Q/K337A/S314E-FVII, F374Y/L305V/E296V/ M298Q/K337A-FVII, F374Y/L305V/E296V/M298Q/ S314E-FVII, F374Y/V158D/E296V/M298Q/K337A-FVII, F374Y/V158D/E296V/M298Q/S314E-FVII, F374Y/ L305V/V158D/K337A/S314E-FVII, F374Y/V158D/ M298Q/K337A/S314E-FVII, F374Y/V158D/E296V/ K337A/S314E-FVII, F374Y/L305V/V158D/E296V/ M298Q-FVII, F374Y/L305V/V158D/M298Q/K337A-FVII, F374Y/L305V/V158D/E296V/K337A-FVII, F374Y/ L305V/V158D/M298Q/S314E-FVII, F374Y/L305V/ V158D/E296V/S314E-FVII, F374Y/V158T/E296V/ M298Q/K337A-FVII, F374Y/V158T/E296V/M298Q/ S314E-FVII, F374Y/L305V/V158T/K337A/S314E-FVII, F374Y/V158T/M298Q/K337A/S314E-FVII, F374Y/ V158T/E296V/K337A/S314E-FVII, F374Y/L305V/ V158T/E296V/M298Q-FVII, F374Y/L305V/V158T/ M298Q/K337A-FVII, F374Y/L305V/V158T/E296V/ K337A-FVII, F374Y/L305V/V158T/M298Q/S314E-FVII, F374Y/L305V/V158T/E296V/S314E-FVII, F374Y/E296V/ M298Q/K337A/V158T/S314E-FVII, F374Y/V158D/ E296V/M298Q/K337A/S314E-FVII, F374Y/L305V/ V158D/E296V/M298Q/S314E-FVII, F374Y/L305V/ E296V/M298Q/V158T/S314E-FVII, F374Y/L305V/ E296V/M298Q/K337A/V158T-FVII, F374Y/L305V/ E296V/K337A/V158T/S314E-FVII, F374Y/L305V/ M298Q/K337A/V158T/S314E-FVII, F374Y/L305V/ V158D/E296V/M298Q/K337A-FVII, F374Y/L305V/ V158D/E296V/K337A/S314E-FVII, F374Y/L305V/ V158D/M298Q/K337A/S314E-FVII, F374Y/L305V/ E296V/M298Q/K337A/V158T/S314E-FVII, F374Y/ L305V/V158D/E296V/M298Q/K337A/S314E-FVII,
S52A-Factor VII, 560A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/ V317T-FVII, K143N/N145T/R315N/V317T-FVII; and Factor VII having substitutions, additions or deletions in the amino acid sequence from 233Thr to 240Asn, Factor VII having substitutions, additions or deletions in the amino acid sequence from 304Arg to 329Cys.

In some embodiments, the Factor VIIa polypeptide is human Factor VIIa (hFVIIa), such as recombinantly made human Factor VIIa (rhFVIIa). In other embodiments, the one or more Factor VII polypeptides comprise a Factor VII sequence variant. In some embodiments, the one or more Factor VII polypeptides have a glycosylation different from wild-type Factor VII.

Nanofiltration

The liquid Factor VII composition is subjected to nanofiltration using a nanofilter having a pore size of at the most 80 nm. The pore size of the nanofilter is more particularly at the most 50 nm, e.g. at the most 30 nm, such as in the range of 10-30 nm.

The term "pore size" typically means the size of the smallest viruses that are withheld by the filter.

Examples of suitable commercially available nanofilters are Asahi Planove 15 N, Asahi Planove 20 N, Asahi Planova 35 N, and Asahi Planova 75 N, all from Asahi Chemical, Tokyo, Japan; Millipore NFR, Millipore NFP, Millipore Viresolve 70, and Millipore Viresolve 180, all from Millipore; and Pall DV20, Pall DV 50, Pall Omega VR 100 K; and Bemberg Microporous Membrane-15 nm (BMM-15).

The nanofilter membrane may, e.g., be manufactured from one or more materials selected from cuprammonium regenerated cellulose, hydrophilic polyvinylidene fluoride (PVDF), composite PVDF, surface modified PVDF, polyether sulfone and similar materials. In one embodiment, the material is selected from polyvinylidene fluoride-based materials and polyether sulfone-based materials.

The nanofiltration may be conducted by in the tangential filtration mode or in the dead-end filtration mode as will be understood by the skilled artisan. In one embodiment, the nanofiltration is conducted in the dead-end filtration mode.

The pH value of the liquid Factor VII composition upon nanofiltration is not considered particularly critical. Thus, the pH value is normally given by in view of the conditions applied in the process steps immediately preceding the nanofiltration step. In some embodiments, the pH value is adjusted so that the liquid composition has a pH of in the range of 5.5-10, such as in the range of 7.0-9.5, e.g. in the range of 7.6-9.4, such as in the range of 7.7-9.3, e.g. in the range of 8.0-9.0 or in the range of 8.3-8.7. In one embodiment the pH is in the range of 5-7. In one embodiment the pH is higher than 9.5, such as in the range of 9.5-10.

Furthermore, the concentration of the Factor VII polypeptide in the liquid composition is typically also given by the preceding process steps, but will normally lie in the range of 0.01-5 mg/mL, such as in the range of 0.05-2.0 mg/mL.

Figure 1:
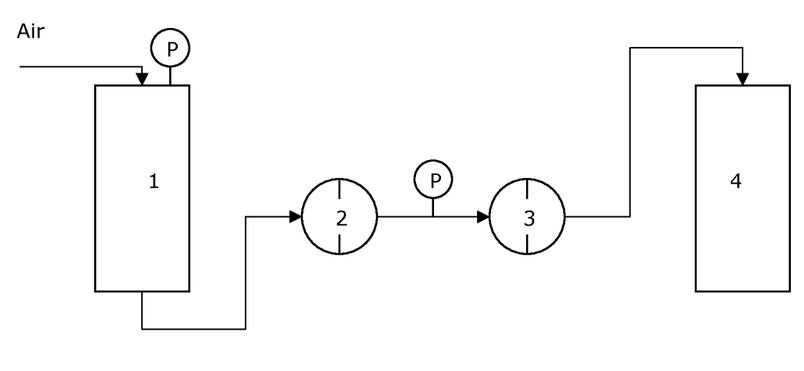

The nanofiltration process may be conducted using a filtration system as illustrated in FIG. 1.

The process may be conducted as in the following illustrative example: The pressure tank (1) is filled with water for injection (WFI), and the pressure in the tank is raised to 3.5 bars before the virus filter (3), and the filter is flushed for 10 minutes. The pressure is reduced to 2 bars and the virus filter (3) is flushed for another 10 minutes. The pressure tank (1) is emptied from WFI and the process is optionally repeated with a buffer before the liquid Factor VII composition is filled into the pressure tank (1). The pressure is raised to 2 bars and is kept substantially constant during the filtration. The virus filter (3) may subsequently be tested for integrity by standard procedures.

The filtrate is collected in a pool tank and can further be processed in order to obtain a pharmaceutical composition comprising a Factor VIIa polypeptide as a drug substance.

This being said, it is typically advantageous to apply a pre-filtration step before the nanofiltration step in order to remove larger particles, aggregates, etc. that would otherwise cause the nanofilter to become clogged. Such a pre-filter typically has a pore size of at in the range of 0.05-0.5 µm. In one embodiment the pre-filter is Millipore NFR filter.

Alternatively to using air pressure, a liquid pump placed after the pressure tank may provide the necessary pressure for the filtration.

If the nanofiltered liquid Factor VII composition comprises inactive Factor VII polypeptides, the composition may subsequently be subjected to an activation step, e.g. as described in Bjørn. S. & Thim, L. Res. Disclosures (1986) 269, 564-565, Pedersen, A. H. & al., Biochemistry (1989), 28, 9331-9336, and Tomokiyo, K. & al., Vox Sang. 84, 54-64 (2003).

Further processing of the composition and final formulation as a pharmaceutical product may be conducted as disclosed in Jurlander, B. & al., Seminars in Thrombosis and Hemostasis 27, 4, 373-383 (2001).

Nanofiltration of Serum-Free Liquid Factor VII Polypeptide Compositions

One separate aspect of the invention, which may include some or all of the above characteristics, relates to a method for removing viruses from a liquid Factor VII composition, said composition comprising one or more Factor VII polypeptides, said liquid composition being substantially serum-free, said method comprising subjecting said solution to nanofiltration using a nanofilter having a pore size of at the most 80 nm.

An attractive variant hereof is the one where the Factor VII polypeptide(s) is/are produced by cell culture in CHO cells, e.g. in CHO cells in a medium free from any components of animal origin.

This aspect of the invention is not particularly limited to liquid Factor VII compositions in which a certain proportion of the Factor VII polypeptide(s) is/are in the activated form. However, the conditions mentioned above for the first aspect of the invention also applies for this, the second aspect of the invention, mutatis mutandis.

Nanofiltration of Liquid Factor VII Polypeptide Compositions Via Particular Filters Another separate aspect of the invention, which may include some or all of the above characteristics, relates to a method for removing viruses from a liquid Factor VII composition, said composition comprising one or more Factor VII polypeptides, said method comprising subjecting said solution to nanofiltration using a nanofilter having a pore size of at the most 80 nm, said nanofilter having a membrane manufactured from one or more materials selected from cuprammonium regenerated cellulose, hydrophilic polyvinylidene fluoride (PVDF), composite PVDF, surface modified PVDF, and polyether sulfone.

In one embodiment, the material is selected from polyvinylidene fluoride-based materials and polyether sulfone-based materials.

This aspect of the invention is not particularly limited to liquid Factor VII compositions in which a certain proportion of the Factor VII polypeptide(s) is/are in the activated form. However, the conditions mentioned above for the first aspect of the invention also applies for this, the third aspect of the invention, mutatis mutandis.

Virus Inactivation by Addition a Detergent

In another aspect, the present invention also relates to a method for inactivating viruses in a liquid Factor VII composition, said composition comprising one or more Factor VII polypeptides, the method comprising the step of combining said composition with a detergent.

In some embodiments, the detergent is selected from non-ionic detergents such as those selected from octylphenoxy polyethoxyethanol, polysorbates, poloxamers, polyoxyethylene alkyl ethers, polyethylene/polypropylene block co-polymers, polyethyleneglycol (PEG), polyoxyethylene stearates, and polyoxyethylene castor oils. Illustrative examples hereof are non-ionic detergents are Triton X-100, Tween®, polysorbate 20, polysorbate 60, polysorbate 80, Brij-35 (polyoxyethylene dodecyl ether), poloxamer 188, poloxamer 407, PEG8000, Pluronic® polyols, polyoxy-23-lauryl ether, Myrj 49, and Cremophor A.

A particularly useful detergent is a octylphenoxy polyethoxyethanol of the formula p-(($CH_3$)$_3$$CH_2$C($CH_2$)$_2$)—$C_6H_4$—O—($CH_2CH_2O$)$_n$—H wherein n is in the range of 5-15, in particular one where n is 9-10, such the detergent Triton X-100.

In one embodiment, the detergent is combined with the liquid Factor VII composition to obtain a concentration of the detergent in the composition of in the range of 0.01-0.5% by weight, such as in the range of 0.05-0.4% by weight, such as in the range of 0.05-0.3% by weight, such as in the range of 0.05-0.2% by weight, such as in the range of 0.05-0.1% by weight.

In a further embodiment, the detergent is combined with the composition at a temperature of in the range of 2-12° C., such as in the range of 2-9° C.

For most purposes, it is found undesirable to include a trialkylphosphate detergent, thus, the detergent may be substantially free of trialkylphosphate solvents such as tri(n-butyl)phosphate.

In one particular embodiment, the method comprises the steps of combining the Factor VII polypeptide composition with Triton X-100 to a concentration of 0.05-0.2% by weight at a temperature in the range of 2-9° C., with the proviso that detergent is substantially free of trialkylphosphate solvents such as tri(n-butyl)phosphate.

This aspect of the invention is not particularly limited to liquid Factor VII compositions in which a certain proportion of the Factor VII polypeptide(s) is/are in the activated form. However, the conditions mentioned above for the first aspect of the invention also applies for this, the fourth aspect of the invention, mutatis mutandis.

Combination of Virus Inactivation Steps

In a still further aspect, the present invention relates to a method for high-level elimination of the presence of active viruses in a liquid Factor VII composition, the method comprising the steps of (i) inactivating viruses by the method defined under "Virus inactivation by addition a detergent", and (ii) removing viruses by the any of the methods defined herein under "Nanofiltration", in any order.

In one embodiment, the step of inactivating viruses precedes the step of removing viruses.

Even though the individual steps are believed to be sufficient for the purpose of eliminating the presence of active viruses, the two methods can be considered as at least partially "orthogonal" in the sense that certain viruses may be more difficult to eliminate by one of the methods, whereas the same of the certain viruses can more easily be eliminated by the other method, and vice versa. Thus, combination of the two methods will provide an even higher level of safety for the patient for which the Factor VII polypeptide is intended, and not the least for the medical doctor prescribing the Factor VII polypeptide medicament, and for the regulatory authorities approving the medicament. Thus, the combination of the two methods may have a high commercial value.

As described above the present invention relates to the removal or inactivation of virus particles. The reduction of the amount of virus particles at a particular process step is usually described in log-units (log 10 logarithm, or $log_{10}$), wherein the reduction factor is calculated as the amount of virus particles after the step relative to the amount of virus particles before the process step.

E.g. if $10^6$ virus particles are found before a step and $10^2$ are found after the step, the reduction is $10^4$, or 4 $log_{10}$.

The total reduction of virus particles from the complete process is described in the same way and may be calculated by addition of the virus clearance from each step in the process, the word "clearance" meaning both removal of virus and inactivation of virus For a specific virus clearance step to be effective, it is preferred to have a virus reduction of at least 4 $\log_{10}$.

In one embodiment of the present invention, a filtration step reduces the amount of virus particles with at least about 4 $\log_{10}$. In one embodiment of the present invention, a filtration step reduces the amount of virus particles with at least about 5 $\log_{10}$.

In one embodiment of the present invention, a step of combining said FVII composition with a detergent inactivates at least about 4 $\log_{10}$ of virus. In one embodiment of the present invention, a step of combining said FVII composition with a detergent inactivates at least about 5 $\log_{10}$ of virus.

The determination of the amount of virus particles is known to the person skilled in the art and may be measured in standard $TCID_{50}$ assays (Tissue culture infectious dose 50% endpoint per mL), plaque assays or PCR assays. $TCID_{50}$ and plaque assays may be used to measure the concentration of infectious particles, whereas the PCR assays may be used to measure both infectious and non-infectious inactivated virus particles

Embodiments of the Present Invention

1. A method for removing viruses from a liquid Factor VII composition, said composition comprising one or more Factor VII polypeptides, at least 5% of said one or more Factor VII polypeptides being in the activated form, said method comprising subjecting said solution to nanofiltration using a nanofilter having a pore size of at the most 80 nm.

2. The method according to embodiment 1, wherein as at least 7%, e.g. at least 10%, of the one or more Factor VII polypeptides are in the activated form.

3. The method according to embodiment 1, wherein the activated form of the Factor VII polypeptide represents 5-70%, such as 7-40%, e.g. 10-30%, of the mass of the one or more Factor VII polypeptides.

4. The method according to embodiment 1, wherein the activated form of the Factor VII polypeptide represents 50-100%, such as 70-100%, e.g. 80-100%, of the mass of the one or more Factor VII polypeptides.

5. The method according to embodiment 1, wherein the activated form of the Factor VII polypeptide represents 20-80%, such as 30-70%, e.g. 30-60%, of the mass of the one or more Factor VII polypeptides.

6. The method according to any of the preceding embodiments, wherein the liquid composition has a pH of in the range of 7.0-9.5, e.g. in the range of 7.6-9.4, such as in the range of 7.7-9.3, e.g. in the range of 8.0-9.0 or in the range of 8.3-8.7.

7. The method according to any of the preceding embodiments, wherein the concentration of the Factor VII polypeptide(s) in the liquid composition is in the range of 0.01-5 mg/mL, such as in the range of 0.05-2.0 mg/mL.

8. The method according to any of the preceding embodiments, wherein the pore size of the nanofilter is at the most 50 nm, e.g. at the most 30 nm, such as in the range of 10-30 nm.

9. The method according to any of the preceding embodiments, wherein the membrane of the nanofilter is manufactured from one or more materials selected from cuprammonium regenerated cellulose, hydrophilic polyvinylidene fluoride (PVDF), composite PVDF, surface modified PVDF, and polyether sulfone.

10. The method according to any of the preceding embodiments, wherein the liquid Factor VII composition is obtained, or originates, from a cell culture supernatant.

11. The method according to any of the preceding embodiments, wherein the liquid composition is substantially serum-free.

12. The method according to any of the embodiments 1-10, wherein the Factor VII polypeptide(s) is/are produced by cell culture in the presence of bovine or foetal calf serum.

13. The method according to any of the preceding embodiments, wherein the Factor VII polypeptide(s) is/are produced by cell culture in CHO cells.

14. The method according to embodiment 13, wherein the Factor VII polypeptide(s) is/are produced by cell culture in CHO cells, in a medium free from any components of animal origin.

15. A method for removing viruses from a liquid Factor VII composition, said composition comprising one or more Factor VII polypeptides, said liquid composition being substantially serum-free, said method comprising subjecting said solution to nanofiltration using a nanofilter having a pore size of at the most 80 nm.

16. The method according to embodiment 15, wherein the liquid Factor VII composition is obtained, or originates, from a cell culture supernatant.

17. The method according to any of the embodiments 15-16, wherein the Factor VII polypeptide(s) is/are produced by cell culture in CHO cells.

18. The method according to embodiment 17, wherein the Factor VII polypeptide(s) is/are produced by cell culture in CHO cells, in a medium free from any components of animal origin.

19. The method according to any of the embodiment 15-18, wherein at least 5% of said one or more Factor VII polypeptides are in the activated form.

20. The method according to any of the embodiments 15-19, wherein the liquid composition has a pH of in the range of 7.0-9.5, e.g. in the range of 7.6-9.4, such as in the range of 7.7-9.3, e.g. in the range of 8.0-9.0 or in the range of 8.3-8.7.

21. The method according to any of the embodiments 15-20, wherein the concentration of the Factor VII polypeptide(s) in the liquid composition is in the range of 0.01-5 mg/mL, such as in the range of 0.05-2.0 mg/mL.

22. The method according to any of the embodiments 15-21, wherein the pore size of the nanofilter is at the most 50 nm, e.g. at the most 30 nm, such as in the range of 10-30 nm.

23. The method according to any of the embodiments 15-22, wherein the membrane of the nanofilter is manufactured from one or more materials selected from cuprammonium regenerated cellulose, hydrophilic polyvinylidene fluoride (PVDF), composite PVDF, surface modified PVDF, and polyether sulfone.

24. A method for removing viruses from a liquid Factor VII composition, said composition comprising one or more Factor VII polypeptides, said method comprising subjecting said solution to nanofiltration using a nanofilter having a pore size of at the most 80 nm, said nanofilter having a membrane manufactured from one or more materials selected from cuprammonium regenerated cellulose, hydrophilic polyvinylidene fluoride (PVDF), composite PVDF, surface modified PVDF, and polyether sulfone.

25. The method according to embodiment 24, wherein the material is selected from polyvinylidene fluoride-based materials and polyether sulfone-based materials.
26. A method according to any of the embodiments 24-25, wherein at least 5% of the one or more Factor VII polypeptides is/are in the activated form.
27. The method according to any of the embodiments 24-26, wherein the liquid composition has a pH of in the range of 7.0-9.5, e.g. in the range of 7.6-9.4, such as in the range of 7.7-9.3, e.g. in the range of 8.0-9.0 or in the range of 8.3-8.7.
28. The method according to any of the embodiments 24-27, wherein the concentration of the Factor VII polypeptide(s) in the liquid composition is in the range of 0.01-5 mg/mL, such as in the range of 0.05-2.0 mg/mL.
29. The method according to any of the embodiments 24-28, wherein the pore size of the nanofilter is at the most 50 nm, e.g. at the most 30 nm, such as in the range of 10-30 nm.
30. The method according to any of the embodiments 24-29, wherein the liquid Factor VII composition is obtained, or originates, from a cell culture supernatant.
31. The method according to any of the embodiments 24-30, wherein the liquid composition is substantially serum-free.
32. The method according to any of the embodiments 24-31, wherein the Factor VII polypeptide(s) is/are produced by cell culture in the presence of bovine or foetal calf serum.
33. The method according to any of the embodiments 24-32, wherein the Factor VII polypeptide(s) is/are produced by cell culture in CHO cells.
34. The method according to embodiment 33, wherein the Factor VII polypeptide(s) is/are produced by cell culture in CHO cells, in a medium free from any components of animal origin.
35. A method for inactivating viruses in a liquid Factor VII composition, said composition comprising one or more Factor VII polypeptides, the method comprising the step of combining said composition with a detergent.
36. The method according to embodiment 35, wherein the detergent is a octylphenoxy polyethoxyethanol of the formula p-$((CH_3)_3CH_2C(CH_2)_2)$—$C_6H_4$—O—$(CH_2CH_2O)_n$—H wherein n is in the range of 5-15.
37. The method according to embodiment 36, wherein the detergent is one where n is 9-10, such as Triton X-100.
38. The method according to embodiment 35, wherein the detergent is selected from the list consisting of Tween®, polysorbate 20, polysorbate 60, and polysorbate 80.
39. The method according to any of the embodiment 35-38, wherein the detergent is combined with the liquid Factor VII composition to obtain a concentration of the detergent in the composition of in the range of 0.01-0.3% by weight, such as in the range of 0.05-0.2% by weight.
40. The method according to any of the embodiments 35-39, wherein the detergent is combined with the composition at a temperature of in the range of 2-12° C., such as in the range of 2-9° C.
41. The method according to any of the embodiments 35-40, wherein the detergent is substantially free of trialkylphosphate solvents such as tri(n-butyl)phosphate.
42. A method for high-level elimination of the presence of active viruses in a liquid Factor VII composition, the method comprising the steps of (i) inactivating viruses by the method defined in any of the embodiments 35-41, and (ii) removing viruses by the any of the methods defined in any of the embodiments 1-35, in any order.
43. The method according to embodiment 42, wherein the step of inactivating viruses precedes the step of removing viruses.

EXAMPLES

Example 1

Serum-Free Production of Factor VII

The following experiment was performed to produce Factor VII in large pilot-scale culture.

A CHO K1 cell line transformed with a Factor VII-encoding plasmid was adapted to growth in suspension culture in a medium free of animal derived components. A bank of the adapted cells was frozen. Cells from the bank were propagated in spinner bottles in suspension culture in medium free of animal derived components. As the cell number increased, the volume was gradually increased by addition of new medium. When the volume had reached 4 L, and the cell number had reached≈$0.8*10^6$/ml, the contents of the spinner bottles were transferred into a 50 L stirred tank reactor (seed reactor). As the cell number increased in the 50 L reactor, the volume was gradually increased by addition of new medium. When the volume had reached 50 L, and the cell number had reached≈$1\times10^6$/ml, the contents of the 50 L reactor were transferred into a 500 L stirred tank reactor (production reactor). The 500 L reactor contained macroporous Cytopore 1 carriers (Amersham Biosciences) within which the cells became immobilized within 24 hours after inoculation. The volume in the 500 L reactor was gradually increased by addition of new medium as the cell number increased. When the volume had reached 450 L, and the cell number had reached≈$2\times10^6$/ml, the production phase was initiated and a medium change was performed every 24 hours: Agitation was stopped to allow for sedimentation of the cell-containing carriers, and 80% of the culture supernatant was then harvested and replaced with new medium. The harvested culture supernatant was filtered to remove non-trapped cells and cell debris and was then transferred for further processing. The 50 L as well as the 500 L bioreactor was instrumented for control of temperature, dissolved oxygen (sparging of oxygen through microsparger), agitation rate, headspace aeration rate and pH (downwards control by addition of $CO_2$ gas to headspace). Furthermore, the 500 L bioreactor was instrumented for control of dissolved $CO_2$. Online $CO_2$ measurement was performed by means of an YSI 8500 $CO_2$-instrument. The level of $CO_2$ was controlled by sparging of atmospheric air into the liquid through a tube according to the $CO_2$ signal. The sparging rate was set to 0 L/min per L of culture liquid when the $CO_2$ concentration was at or below the set-point, and to 0.01-0.05 L/min per L of culture liquid when the $CO_2$ concentration was above the set-point. The set-point for dissolved $CO_2$ was 160 mmHg. As mentioned, no base was added to the bioreactor to control pH upwards. During the production phase the cell density reached $1$-$2\times10^7$ cells/ml, and the Factor VII concentration in the daily harvest 10-20 mg/L. The $pCO_2$ was maintained within the range of 150-170 mmHg. The pH was kept above 6.70, even though no base was added.

Example 2

Filtration of Eluate from the Capture Step

Protein solution to be filtered: 25 L of FVII solution from the capture step, with the following characteristics
Concentration of FVII/FVIIa: 630 mg/L
1.7% of oxidized forms of FVII
Degree of activation (i.e. percentage of FVIIa): not analysed
Degradation: <2.2%

The filtration was conducted essentially as described herein with reference to FIG. 1:
Filter: Millipore NFR, 0.08 m2
Pressure: 2 bar
Properties of the Filtrate:
Concentration of FVII/FVIIa: 610 mg/L, i.e.: yield of FVII: 96.8%
1.5% of oxidized forms of FVII
Degree of activation (i.e. percentage of FVIIa): not analysed.
Degradation: <2.2%

Example 3

Filtration of Eluate from the Capture Step

Protein solution to be filtered: 185 ml of FVII solution from the capture step, with the following characteristics
Concentration of FVII/FVIIa: 82 mg/L
3.4% of oxidized forms of FVII
Degree of activation (i.e. percentage of FVIIa): 19%.
Degradation: <3%
The filtration was conducted essentially as described herein with reference to FIG. 1:
Filter: Pall DV50, 0.0017 m2
Pressure: 2 bar
Properties of the Filtrate:
Concentration of FVII/FVIIa: 77.1 mg/L, i.e.: yield of FVII: 94%
4.1% of oxidized forms of FVII
Degree of activation (i.e. percentage of FVIIa): 20%.
Degradation: <3%

Example 4

Filtration of Eluate from the Capture Step

Protein solution to be filtered: 108 ml step 1 eluate with the following characteristics:
Concentration of FVII/FVIIa: 320 mg/L
3.7% of oxidized forms of FVII
Degree of activation (i.e. percentage of FVIIa) 3.3%
Degradation: <0.5%
The filtration was conducted essentially as described herein with reference to FIG. 1:
Filter: Asahi Planova 20 N, 0.001 m2
Pressure: 0.8 bar
Properties of the Filtrate:
Concentration of FVII/FVIIa: 310 mg/L, i.e.: yield of FVII: 100%
3.7% of oxidized forms of FVII
Degree of activation (i.e. percentage of FVIIa): not analysed,
Degradation: <0.5%

Example 5

Filtration of FVII Bulk Drug Substance

Protein solution to be filtered: 98 ml of FVIIa bulk substance, with the following characteristics
Concentration of FVII/FVIIa: 1460 mg/L
2.1% of oxidized forms of FVII
Degree of activation (i.e. percentage of FVIIa): >90%.
Degradation: 11.9%
The filtration was conducted essentially as described herein with reference to FIG. 1:
Filter: Millipore NFP, 0.0017 m2
Pressure: 2 bar
Properties of the Filtrate:
Concentration of FVII/FVIIa: 1320 mg/L, i.e.: yield of FVII: 90.4%
2.3% of oxidized forms of FVII
Degree of activation (i.e. percentage of FVIIa): not analysed, as the degree of activation in the solution to be filtered is 98%
Degradation: 12.3%

Example 6

Virus Removal 50 ml of a Factor VII polypeptide solution (see Example 1) from the capture step comprising a Murine Leukemia Virus, titer YY plaque-forming units (pfu).
The filtration is conducted essentially as described herein with reference to FIG. 1:
Filter: Millipore NFR, yy cm2
Pressure: YY bar
Virus titer in the filtrate: xx pfu
Calculated clearance factor: xx.

The invention claimed is:

1. A method for removing viruses from a liquid composition of recombinant Factor VII comprising one or more Factor VII polypeptides having a concentration in the range of 0.01 to 5 mg/mL, the method comprising subjecting the liquid composition to nanofiltration using a nanofilter having a pore size of 80 nm or less, wherein 50-100% of the Factor VII polypeptides in the composition subjected to the nanofilter are in an activated form (FVIIa) prior to nanofiltration.

2. The method according to claim 1, wherein the liquid composition has a pH of in the range of 7.0-9.5.

3. The method according to claim 2, wherein the pH is in the range of 8.3-8.7.

4. The method according to claim 1, wherein the pore size of the nanofilter is 50 nm or less.

5. The method according to claim 1, wherein the membrane of the nanofilter is manufactured from one or more materials selected from the group consisting of: cuprammonium regenerated cellulose, hydrophilic polyvinylidene fluoride (PVDF), composite PVDF, surface modified PVDF, and polyether sulfone.

6. The method according to claim 1, wherein the pore size of the nanofilter is in the range of 10-30 nm.

7. The method according to claim 1, wherein the liquid Factor VII composition is obtained from a cell culture supernatant.

8. The method according to claim 1, wherein the liquid composition is serum-free.

9. The method according to claim 1, wherein the Factor VII polypeptide(s) is/are produced by cell culture in the presence of bovine or foetal calf serum.

10. The method according to claim 1, wherein the Factor VII polypeptide(s) is/are produced by cell culture in Chinese Hamster Ovary (CHO) cells in a medium free from any components of animal origin.

11. The method according to claim 1, wherein the concentration of the Factor VII polypeptide(s) in the liquid composition is in the range of 0.05-2.0 mg/mL.

12. A method for removing viruses from a liquid composition of recombinant Factor VII comprising one or more Factor VII polypeptides having a concentration in the range of 0.01 to 5 mg/mL, wherein 50-100% of the Factor VII polypeptides in the composition are in an activated form (FVIIa) prior to nanofiltration, the method comprising the steps of (i) combining the composition with a detergent, and (ii) subjecting the solution to nanofiltration using a nanofilter having a pore size of 80 nm or less.

13. The method of claim 1, wherein 70-100% of the Factor VII polypeptides in the composition subjected to the nanofilter are the activated form of Factor VII.

14. The method of claim 1, wherein 80-100% of the Factor VII polypeptides in the composition subjected to the nanofilter are the activated form of Factor VII.

15. A method for removing viruses from a liquid composition of recombinant Factor VII comprising one or more Factor VII polypeptides having a concentration in the range of 0.01 to 5 mg/mL, the method comprising subjecting the liquid composition to nanofiltration using a nanofilter having a pore size of 50 nm or less, wherein 50-100% of the Factor VII polypeptides in the composition subjected to the nanofilter are in an activated form (FVIIa) prior to nanofiltration.

\* \* \* \* \*

(12) INTER PARTES REVIEW CERTIFICATE (2910th)
United States Patent (10) Number: US 9,102,762 K1
Christensen et al. (45) Certificate Issued: Nov. 14, 2022

(54) VIRUS FILTRATION OF LIQUID FACTOR VII COMPOSITIONS

(75) Inventors: Jesper Christensen; Erik Halkjaer; Turid Preuss; Thomas Budde Hansen; Lene Vaedele Madsen Tomoda; Nina Johansen (73) Assignee: NOVO NORDISK HEALTHCARE AG

Trial Number:

IPR2017-00028 filed Oct. 7, 2016

Inter Partes Review Certificate for:

Patent No.: 9,102,762
Issued: Aug. 11, 2015
Appl. No.: 13/349,980
Filed: Jan. 13, 2012

The results of IPR2017-00028 are reflected in this inter partes review certificate under 35 U.S.C. 318(b).

INTER PARTES REVIEW CERTIFICATE
U.S. Patent 9,102,762 K1
Trial No. IPR2017-00028
Certificate Issued Nov. 14, 2022

AS A RESULT OF THE INTER PARTES REVIEW PROCEEDING, IT HAS BEEN DETERMINED THAT:

Claims 1-15 are found patentable.

\* \* \* \* \*